US008530150B2

(12) United States Patent
Bates et al.

(10) Patent No.: US 8,530,150 B2
(45) Date of Patent: Sep. 10, 2013

(54) DETECTION OF RISK OF PRE-ECLAMPSIA

(75) Inventors: David Owen Bates, Bristol (GB);
Victoria Louise Bills, Bristol (GB);
Steven James Harper, Bristol (GB);
Yan Qiu, Bristol (GB)

(73) Assignee: The University of Bristol, Bristol (GB)

( * ) Notice: Subject to any disclaimer, the term of this patent is extended or adjusted under 35 U.S.C. 154(b) by 368 days.

(21) Appl. No.: 12/889,571

(22) Filed: Sep. 24, 2010

(65) Prior Publication Data

US 2011/0076259 A1    Mar. 31, 2011

Related U.S. Application Data

(60) Provisional application No. 61/245,893, filed on Sep. 25, 2009.

(51) Int. Cl.
*C12Q 1/00* (2006.01)
(52) U.S. Cl.
USPC .............................................. 435/4; 435/69.6
(58) Field of Classification Search
CPC ....................................................... C12Q 1/00
USPC .................................................. 435/4, 69.6
See application file for complete search history.

(56) References Cited

U.S. PATENT DOCUMENTS

2004/0126828 A1    7/2004   Karumanchi et al. ....... 435/7.92

FOREIGN PATENT DOCUMENTS

| WO | WO 03/012105 | 2/2003 |
| WO | WO 2008/110777 | 9/2008 |

OTHER PUBLICATIONS

Alberry, et al. (2007) "Management of fetal growth restriction." *Arch. Dis. Child Fetal Neonatal Ed.*, Jan; 92(1):F62-F67.
Anthony, et al. (1997) "Variation in detection of VEGF in maternal serum by immunoassay and the possible influence of binding proteins." *Ann. Clin. Biochem.*, May; 34(Pt 3):276-280.
Bates, et al. (2002) "VEGF165b, an inhibitory splice variant of vascular endothelial growth factor, is down-regulated in renal cell carcinoma." *Cancer Res.*, Jul. 15; 62(14): 4123-4131.
Bates, et al. (2006) "The endogenous anti-angiogenic family of splice variants of VEGF, VEGFxxxb, are down-regulated in pre-eclamptic placentae at term." *Clin. Sci.* (London), May; 110(5):575-585.
Baumwell, et al. (2007) "Pre-eclampsia: clinical manifestations and molecular mechanisms." *Nephron Clin. Pract.*, 106(2):c72-81.
Bills, et al. (2009) "Failure to up-regulate $VEGF_{165}b$ in maternal plasma is a first trimester predictive marker for pre-eclampsia." *Clin. Sci.* (London), Feb; 116(3-4):265-272.
Brockelsby, et al. (1999) "VEGF via VEGF receptor-1 (Flt-1) mimics preeclamptic plasma in inhibiting uterine blood vessel relaxation in pregnancy: implications in the pathogenesis of preeclampsia." *Lab. Invest.*, Sep; 79(9):1101-1111.
Duley, et al. (2001) "Antiplatelet drugs for prevention of pre-eclampsia and its consequences: systematic review." *Br. Med. J.*, Feb. 10; 322(7282):329-333.
Ferrara, N. (2004) "Vascular endothelial growth factor: basic science and clinical progress," *Endocr. Rev.*, Aug; 25 (4):581-611.
Glass, et al. (2006) "The anti-angiogenic VEGF isoform $VEGF_{165}b$ transiently increases hydraulic conductivity, probably through VEGF receptor 1 in vivo." *J. Physiol.*, Apr. 1; 572(Pt 1):243-257.
Khan, et al. (2006) "WHO analysis of causes of maternal death: a systematic review." *Lancet*, Apr. 1; 367(9516):1066-1074.
Konopatskaya, et al. (2006) "VEGF165b, an endogenous C-terminal splice variant of VEGF, inhibits retinal neovascularization in mice." *Mol. Vis.*, May 26; 12:626-632.
Lee, et al. (2007) "The levels of circulating vascular endothelial growth factor and soluble Flt-1 in pregnancies complicated by preeclampsia." *J. Korean Med. Sci.*, Feb; 22(1):94-98.
Levine, et al. (2004) "Circulating angiogenic factors and the risk of preeclampsia." *N. Engl. J. Med.*, Feb. 12; 350(7):672-683.
Levine, et al. (2006) "Soluble endoglin and other circulating antiangiogenic factors in preeclampsia." *N. Engl. J. Med.*, Sep. 7; 355(10):992-1005.
Li, et al. (2007) "Recombinant vascular endothelial growth factor 121 attenuates hypertension and improves kidney damage in a rat model of preeclampsia." *Hypertension*, Oct; 50(4):686-692.
Livingston, et al. (2000) "Reductions of vascular endothelial growth factor and placental growth factor concentrations in severe preeclampsia." *Am. J. Obstet. Gynecol.*, Dec; 183(6):1554-1557.
Lyall, et al. (1997) "Placental expression of vascular endothelial growth factor in placentae from pregnancies complicated by pre-eclampsia and intrauterine growth restriction does not support placental hypoxia at delivery." *Placenta*, May; 18(4):269-276.
McKeeman, et al. (2004) "Soluble vascular endothelial growth factor receptor-1 (sFlt-1) is increased throughout gestation in patients who have preeclampsia develop." *Am. J. Obstet. Gynecol.*, Oct; 191(4):1240-1246.
Maynard, et al. (2005) "Soluble Fms-like tyrosine kinase 1 and endothelial dysfunction in the pathogenesis of preeclampsia." *Pediatr. Res.*, May; 57(5 Pt 2):1R-7R.
Maynard, et al. (2003) "Excess placental soluble fms-like tyrosine kinase 1 (sFlt1) may contribute to endothelial dysfunction, hypertension, and proteinuria in preeclampsia." *J. Clin. Invest.*, 111(5):649-658.
Murakami, et al. (2005) "Exogenous vascular endothelial growth factor can induce preeclampsia-like symptoms in pregnant mice." *Semin. Thromb. Hemost.*, Jun: 31(3):307-313.
Nadar, et al. (2005) "Plasma markers of angiogenesis in pregnancy induced hypertension." *Thromb. Haemost.*, Nov; 94(5):1071-1076.

(Continued)

*Primary Examiner* — Bin Shen
(74) *Attorney, Agent, or Firm* — Harness, Dickey & Pierce, P.L.C.; J. Timothy Keane; Kisuk Lee

(57) ABSTRACT

A method of detecting a risk of a pregnant female mammal developing pre-eclampsia or a complication linked thereto, or of a fetus of the pregnant female mammal developing a fetal or neonatal deficiency linked to maternal pre-eclampsia, comprises detecting the level of a $VEGF_{xxx}b$ in a sample from the pregnant female mammal at less than about 24 weeks of gestation and comparing the detected level with a reference level. A reduced level in the sample from the pregnant female mammal is indicative of a risk of the pregnant female mammal developing pre-eclampsia or a complication linked thereto or of the fetus developing the fetal or neonatal deficiency linked to maternal pre-eclampsia.

13 Claims, 4 Drawing Sheets

(56) References Cited

OTHER PUBLICATIONS

Perrin, et al. (2005) "Diabetic retinopathy is associated with a switch in splicing from anti- to pro-angiogenic isoforms of vascular endothelial growth factor." *Diabetologia*, Nov; 48(11):2422-2427.

Pritchard-Jones, et al. (2007) "Expression of VEGF(xxx)b, the inhibitory isoforms of VEGF, in malignant melanoma." *Br. J. Cancer*, Jul. 16;97(2):223-230.

Qiu, et al. (2008) "Mammary alveolar development during lactation is inhibited by the endogenous antiangiogenic growth factor isoform, VEGF165b." *FASEB J.*, Apr; 22(4):1104-1112.

Rennel, et al. (2008) "The endogenous anti-angiogenic VEGF isoform, VEGF(165)b inhibits human tumour growth in mice." *Br. J. Cancer*, Apr. 8; 98(7):1250-1257.

Schumacher, et l. (2007) "Impaired glomerular maturation and lack of VEGF165b in Denys-Drash syndrome." *J. Am. Soc. Nephrol.*, Mar; 18(3):719-729.

Sgambati, et al. (2004) "VEGF expression in the placenta from pregnancies complicated by hypertensive disorders." *Br. J. Obstet. Gynaecol.*, Jun; 111(6):564-570.

Stepan, H. (2009) "Angiogenic factors and pre-eclampsia: An early marker is needed." *Clin. Sci., Portland Press LTD, GBR LNKD*, Feb; 116(3)231-232.

Varey, et al. (2008) "VEGF(165)b, an antiangiogenic VEGF-A isoform, binds and inhibits bevacizumab treatment in experimental colorectal carcinoma: balance of pro- and antiangiogenic VEGF-A isoforms has implications for therapy." *Br. J. Cancer*, Apr. 22; 98(8):1366-1379.

Venkatesha, et al. (2006) "Soluble endoglin contributes to the pathogenesis of preeclampsia." *Nat. Med.*, Jun; 12(6):642-649.

Woolard, et al. (2004) "$VEGF_{165}b$, an inhibitory vascular endothelial growth factor splice variant: mechanism of action, in vivo effect on angiogenesis and endogenous protein expression." *Cancer Res.*, Nov. 1; 64(21):7822-7835.

Zhou, et al. (1997) "Preeclampsia is associated with failure of human cytotrophoblasts to mimic a vascular adhesion phenotype. One cause of defective endovascular invasion in this syndrome?" *J. Clin. Invest.*, May 1; 99(9):2152-2164.

International Search Report in PCT/GB2009/051263: dated Aug. 3, 2010.

DETECTION OF RISK OF PRE-ECLAMPSIA

CROSS-REFERENCE TO RELATED APPLICATIONS

This application claims the benefit of U.S. provisional application Ser. No. 61/245,893, filed Sep. 25, 2009. The entire disclosure of the application is hereby incorporated by reference.

FIELD

The present invention relates to a method for the detection of a risk of pre-eclampsia, and to materials and kits for use in the method.

BACKGROUND

The disclosures of all publications mentioned below, whether patent or non-patent documents, are incorporated herein by reference.

Pre-eclampsia is a pregnancy-related disease characterised by hypertension, proteinuria and oedema. It is responsible for around 12% of the world's annual 514,000 maternal deaths [Reference 1]. Aside from maternal and fetal death, the condition can also result in intra-uterine growth restriction, seizures (eclampsia), renal or liver failure, and placental abruption. Despite much investigation, the pathological processes underlying this disease are still largely undiscovered. Recent investigation had focussed on defective placental implantation as an important aetiological factor, with the resulting release of placentally derived circulating factors, which cause endothelial dysfunction [References 2, 3, 4]. At the microvascular level, there is a state of vasoconstriction from smooth muscle contraction, increased vascular permeability and anti-angiogenesis [Reference 5], which correspond to the clinical findings of high blood pressure, oedema and a characteristically small placenta at delivery of the baby.

The vascular endothelial growth factor (VEGF) family is thought to be one of the important molecular systems involved in the pathogenesis of pre-eclampsia. Conventional VEGF, also known as VEGF-A, is made up of 6 different isoforms formed from alternative exon splicing resulting in proteins of varying amino acid length, termed $VEGF_{xxx}$. $VEGF_{165}$ is the most common isoform of $VEGF_{xxx}$, and consists of 165 amino acids. $VEGF_{165}$ acts via its receptor VEGFR-2 to increase vascular permeability, vasodilatation and angiogenesis [Reference 6]. Endogenous alternative splicing of the VEGF receptor results in soluble VEGFR-1 (also known as soluble fms-like tyrosine kinase 1 or sFlt-1), which binds to VEGF and inhibits its function [Reference 6]. High levels of sFlt-1 have been documented in pre-eclampsia [Reference 7].

VEGF levels in pre-eclampsia have been measured by a number of techniques, with conflicting results according to the technique used. When measured by commercial sandwich Enzyme Linked ImmunoSorbent Assays (ELISAs)—which has been proposed to measure only the free, unbound forms of VEGF-levels appear to be reduced in pre-eclampsia [References 8, 9]. When measured by radioimmunoassay (RIA) or competitive enzyme immuno assay (cEIA), VEGF levels are shown to substantially increase. This discrepancy has been proposed to be due to these latter two methods not being affected by circulating binding proteins [References 10, 11].

In 2002, an alternative family of VEGF-A isoforms were identified, termed $VEGF_{xxx}b$. These are the same size as conventional VEGF-A but are alternatively spliced in exon 8 [Reference 12]. This alternative splice site selection results in an alternate 6 amino acid C terminus, which affects the property of the isoforms. $VEGF_{165}b$ is the most widely studied of these isoforms. $VEGF_{165}b$ has been shown to inhibit the effects of $VEGF_{165}$ by binding to its principal receptor VEGFR-2 and preventing it from exerting its physiological effects such as endothelial cell proliferation and migration. $VEGF_{165}b$ also binds to and activates Flt-1 (VEGFR-1), resulting in a transient increase in capillary hydraulic conductivity but no sustained increase in permeability, in contrast with $VEGF_{165}$ [Reference 13].

WO03/012105 describes the use of $VEGF_{165}b$ inhibitors, for example anti-$VEGF_{165}b$ antibodies, to treat pre-eclampsia associated with a lack of $VEGF_{165}$-mediated vasodilation. The rationale underlying this treatment is explained at page 23, line 21 to page 24, line 12. However, Bates et al, [Reference 29] report that pre-eclamptic placentae at term have significantly down-regulated levels of $VEGF_{xxx}b$, implying a different mechanism than merely excess $VEGF_{165}b$ expression. Evidence is presented to indicate a significant uncoupling of the splicing regulation of the VEGF isoforms in late pre-eclampsia. It is theorised that such dysregulation of mRNA splicing in VEGF gene expression in pre-eclampsia may be linked to apparent dysregulation of mRNA splicing in expression of the VEGFR (VEGF receptor) gene, also observed in human pre-eclampsia.

We have now surprisingly found that a delay in the up-regulation of $VEGF_{xxx}b$, for example $VEGF_{165}b$, in the pregnant maternal plasma from the non-pregnant level to a higher concentration is an early marker indicative of risk of pre-eclampsia later in the pregnancy. This longitudinal parameter can therefore be used as the basis for a predictive assay for risk of pre-eclampsia.

It follows that clinical intervention in about the first trimester of the pregnancy to restore maternal plasma concentration of $VEGF_{xxx}b$, for example $VEGF_{165}b$, to or towards normal levels will provide a valuable treatment for reducing a risk of development of pre-eclampsia later in the pregnancy or for delaying onset of pre-eclampsia, thereby improving the prospects of fetal and maternal survival. Aspects of this study are described in Bills et al, Clinical Science (2009) 116, pages 265-272 ("Failure to Up-Regulate $VEGF_{165}b$ in Maternal Plasma is a First Trimester Predictive Marker for Pre-Eclampsia"). To the extent that any part of that publication or any related publication prior to the filing of this patent application would otherwise be prior art against the invention under the relevant law, we claim the benefit of any grace period provided by the relevant law.

SUMMARY

According to a first aspect the present invention, there is provided a method of detecting a risk of a pregnant female mammal developing pre-eclampsia or a complication linked thereto, or of a fetus of the pregnant female mammal developing a fetal or neonatal deficiency linked to maternal pre-eclampsia, comprising detecting the level of a $VEGF_{xxx}b$ in a sample from the pregnant female mammal before about the end of the second trimester of the mammal's pregnancy and comparing the detected level with a reference level, a level in the sample of the pregnant female mammal below the reference level being indicative of a risk of the pregnant female mammal developing pre-eclampsia or a complication linked thereto or of the fetus developing the fetal or neonatal deficiency linked to maternal pre-eclampsia.

According to a second aspect of the present invention, there is provided a kit for use in determining an increased risk to a pregnant female mammal of pre-eclampsia or a complication linked thereto or to the fetus of the pregnant female mammal of developing a fetal or neonatal deficiency linked to maternal pre-eclampsia, the kit comprising a reagent for detection of the level of a $VEGF_{xxx}b$ in a sample from the pregnant female mammal. The kit can be used to detect level of $VEGF_{xxx}b$ in the sample before about the end of the second trimester of the mammal's pregnancy, and the detected level is compared with a reference level, a level in the sample below the reference level being indicative of a risk of the pregnant female mammal developing pre-eclampsia or a complication linked thereto or of the fetus developing the fetal or neonatal deficiency linked to maternal pre-eclampsia.

According to a third aspect of the present invention, there is provided a method of reducing the risk of a female mammal developing pre-eclampsia or a complication linked thereto, or of a fetus of the female mammal developing a fetal or neonatal deficiency linked to maternal pre-eclampsia, comprising increasing the level of a $VEGF_{xxx}b$ in the female mammal before about the end of the second trimester of the mammal's pregnancy to a level at which the risk of the pregnant female mammal developing pre-eclampsia or a complication linked thereto or of the fetus developing the fetal or neonatal deficiency linked to maternal pre-eclampsia is reduced. The method of increasing the level of a $VEGF_{xxx}b$ in the female mammal before about the end of the second trimester of the pregnancy can comprise increasing the level of a $VEGF_{xxx}b$ in the female mammal before conception or before pregnancy is confirmed. Usually, treatment of the female to increase the level of the $VEGF_{xxx}b$ will continue at least during the first trimester and optionally also into the second and/or third trimester.

The increasing of the level of a $VEGF_{xxx}b$ in the method according to the third aspect of the present invention can be carried out by administering a $VEGF_{xxx}b$ active agent to the female mammal.

The administration of the $VEGF_{xxx}b$ active agent to the female mammal can be performed in association with other therapeutic or prophylactic treatment for pre-eclampsia and complications linked to pre-eclampsia as described herein. Such other therapeutic or prophylactic treatments include, for example, administration of pharmaceutical compositions (for example, oral compositions containing aspirin) for reducing incidence of pre-eclampsia.

Depending on the results of the risk detection method according to the first aspect of the present invention, the risk reduction method according to the third aspect of the present invention can then be carried out.

The $VEGF_{xxx}b$ can be full $VEGF_{xxx}b$ protein or an anti-angiogenic fragment thereof, or other $VEGF_{xxx}b$ derived or related protein material which is functionally equivalent to full $VEGF_{xxx}b$ protein in relevant respects. The term "$VEGF_{xxx}b$" is to be understood in this manner.

The term "$VEGF_{xxx}b$ active agent" used herein encompasses $VEGF_{xxx}b$ protein material and agents which promote the presence or endogenous expression of $VEGF_{xxx}b$ relative to the untreated subject. Such agents include those described in WO2008/110777 (the disclosure of which is incorporated herein by reference) that favour distal splice site (DSS) splicing during processing of VEGF pre-mRNA transcribed from the C terminal exon 8 of the VEGF-A gene. Such agents can, if desired, be used in association with one or more controlling agents for the splicing which suppresses or inhibits proximal splice site (PSS) splicing during processing of VEGF pre-mRNA transcribed from the C terminal exon 8 of the VEGF-A gene (see WO2008/110777).

According to a fourth aspect of the present invention, there is provided a method of testing a (pregnant or non-pregnant) female mammalian subject for risk of developing pre-eclampsia or a complication linked thereto, the method comprising genotyping the subject to determine a risk of under-expressing $VEGF_{xxx}b$ relative to normal $VEGF_{xxx}b$ level before about 24 weeks of gestation in pregnancy.

Wherever an embodiment, example or preference is described or expressed herein in relation to one aspect of the present invention, it shall be understood that the embodiment, example or preference applies equally to all other aspects of the invention unless this is not technically feasible.

DETAILED DESCRIPTION

Pre-Eclampsia Categories in Humans

Pre-eclampsia in humans can develop as early as 20 weeks of gestation. Pre-eclampsia that develops before about 34 weeks of gestation is normally referred to as "early pre-eclampsia" or "early-onset pre-eclampsia". Pre-eclampsia that develops after about 34 weeks of gestation is normally referred to as "late pre-eclampsia" or "late-onset pre-eclampsia".

In addition, pre-eclampsia can be categorised as "severe pre-eclampsia" according to criteria established by the United Kingdom Royal College of Obstetricians and Gynaecologists. Under these criteria, a patient with "severe pre-eclampsia" will have systolic blood pressure (BP) greater than 169 mmHg or diastolic BP greater than 109 mmHg with proteinuria greater than 1 g/24 h; or will show occurrence of HELLP syndrome (haemolysis, elevated liver enzymes and low platelet count).

The expressions in quotation marks, and like expressions, will be used in these senses in the present application.

In embodiments of the invention, the pre-eclampsia detected or treated can be early pre-eclampsia or later pre-eclampsia, or can be severe pre-eclampsia of either the late or early type.

$VEGF_{xxx}b$ $VEGF_{xxx}b$ can, for example, comprise one or more of $VEGF_{165}b$, $VEGF_{189}b$, $VEGF_{145}b$, $VEGF_{183}b$, $VEGF_{121}b$ and $VEGF_{111}b$. The $VEGF_{xxx}b$ suitably comprises recombinant $VEGF_{xxx}b$, such as recombinant human $VEGF_{xxx}b$ (rh-$VEGF_{xxx}b$).

The $VEGF_{xxx}b$ can comprise $VEGF_{165}b$, e.g., recombinant $VEGF_{165}b$, such as recombinant human $VEGF_{165}b$ (rh$VEGF_{165}b$).

The $VEGF_{xxx}b$ can, for example, consist essentially of $VEGF_{165}b$, e.g., recombinant $VEGF_{165}b$, such as recombinant human $VEGF_{165}b$ (rh$VEGF_{165}b$). The $VEGF_{xxx}b$ may, for example, consist of $VEGF_{165}b$, e.g., recombinant $VEGF_{165}b$, such as recombinant human $VEGF_{165}b$ (rh$VEGF_{165}b$).

Subject

In an embodiment the subject can be a human or non-human mammal.

Besides being useful for human treatment, the present invention is also useful in a range of mammals. Such mammals include non-human primates (e.g., apes, monkeys and lemurs), for example in zoos, companion animals such as cats or dogs, working and sporting animals such as dogs, horses and ponies, farm animals, for example pigs, sheep, goats, deer, oxen and cattle, and laboratory animals such as rodents (e.g., rabbits, rats, mice, hamsters, gerbils or guinea pigs).

In a specific example, the mammal is a human.

When the present invention is applied in humans, the expression "end of the second trimester of the pregnancy" refers to a time at about 24 weeks of gestation, this period being calculated in the conventional manner, namely from the subject's last menstruation. In an embodiment, the detection of the level of a $VEGF_{xxx}b$ in a sample from the pregnant human female is made before about the end of the first trimester of the mammal's pregnancy, namely before about 12 weeks of gestation.

Sample

The sample from the subject can be a sample of body fluid or tissue taken from the subject for analysis. A specific example of such a sample is a sample of a body fluid. The body fluid can, for example, be selected from blood, plasma, serum, saliva, tears, sputum, urine, buccal, cervical or vaginal smears or swabs. A commonly available type of sample is blood or plasma. The detection can be performed in vivo or, more typically, in vitro.

Detection of $VEGF_{xxx}b$ Level

Detection of the level of $VEGF_{xxx}b$ can be performed in any suitable manner, for example by means of assays using antibodies, receptors, binding molecules and the like, or separation methods for proteins based on such factors as molecular weight or isoelectric point or other contributing factors to variances in retention characteristics of different components of a sample on a substrate or column, including but not limited to high pressure liquid chromatography, gel electrophoresis, microfluidic gel-free electrophoresis, Western Blotting or mass spectroscopy. In certain embodiments, the detection can involve the use of antibodies which bind the $VEGF_{xxxb}$. Any of these antibodies, receptors or binding molecules can be labelled with detectable markers (e.g., fluorescent or radioactive or enzyme markers) to allow detection, or can themselves be detectable with labelled secondary antibodies or binding molecules or enzymes. Any of the antibodies, receptors or binding molecules can be either in solution or affixed to a solid support in conventional manner.

Examples of assay methods useful for detecting the $VEGF_{xxx}b$ level in connection with the present invention include, but are not limited to, for example, enzyme immunoassays (EIA) such as enzyme multiplied immunoassay technique (EMIT), enzyme-linked immunosorbent assay (ELISA), IgM antibody capture ELISA (MAC ELISA), microparticle enzyme immunoassay (MEIA), capillary electrophoresis immunoassay (CEIA), radioimmunoassay (RIA), immuno-radiometric assays (IRMA), fluorescence polarisation immunoassay (FPIA), dissociation-enhanced lanthanide fluorescent immunoassay (DELFIA) and chemiluminescence assays (CL).

The assay can be performed in a number of possible ways, as is well known in the art. For example, the $VEGF_{xxx}b$ of the sample can first be immobilised onto a surface (for example, a surface of a well in a plate, a bead surface or a tube surface), whether specifically using a suitable antibody or other specific binding system (sandwich assays) or non-specifically (indirect assays). Any residual unbound $VEGF_{xxx}b$ is removed and the quantitatively detectable marker (label) is then applied specifically to the bound $VEGF_{xxx}b$ via one or more further antibodies or other specific binding system as an intermediate between the $VEGF_{xxx}b$ and the label. Detection of the label is calibrated using quantitatively known standard analogue systems. Examples of such assays are sandwich immunoassays, for example sandwich EIAs such as sandwich ELISAs.

Alternatively, $VEGF_{xxx}b$ or an analogue having similar complementary binding properties can first be immobilised onto the surface, whether specifically using a suitable antibody or other specific binding system or non-specifically, and the sample added in the form of a complex with an anti-$VEGF_{xxx}b$ antibody (which can be specific or non-specific to $VEGF_{xxx}b$) or other binding partner of $VEGF_{xxx}b$ so that the immobilised $VEGF_{xxx}b$ must compete to displace the antibody or other binding partner from the sample $VEGF_{xxx}b$. The extent that it does so is measured by detection of the extent to which the anti-$VEGF_{xxx}b$ antibody or other binding partner of $VEGF_{xxx}b$ is taken up into the immobilised phase after equilibration, for example by detecting a label on the anti-$VEGF_{xxx}b$ antibody or other binding partner of $VEGF_{xxx}b$. The amount of $VEGF_{xxx}b$ in the sample is calculated from the extent to which it was displaced in the competition and the binding partner immobilised. Alternatively, the (unlabelled) anti-$VEGF_{xxx}b$ antibody (which can be specific or non-specific to $VEGF_{xxx}b$) or other binding partner of $VEGF_{xxx}b$ can be immobilised onto the surface and the sample $VEGF_{xxx}b$ and labelled $VEGF_{xxx}b$ added. After equilibration and removal of unbound labelled material, the extent to which the labelled and sample $VEGF_{xxx}b$ have become immobilised is measured by quantification of the bound label, from which the amount of $VEGF_{xxx}b$ in the sample is calculated. Examples of such assays are competitive immunoassays, for example competitive EIS such as competitive ELISAs.

A specific assay method is ELISA, particularly a sandwich ELISA using two antibodies directed to different domains of the $VEGF_{xxx}b$ family or of one or more particular proteins of the family. These domains can, for example, be domains that are found also in proteins of the $VEGF_{xxx}$ family, or can be domains that are specific to the $VEGF_{xxx}b$ family or one or more particular proteins of the family. Typically, the immobilised antibody is a monoclonal antibody specific for a C terminal epitope of $VEGF_{xxx}b$, particularly $VEGF_{165}b$ and the label (e.g., the enzyme horseradish peroxidise) bound to the immobilised antigen via a polyclonal anti-(human VEGF) antibody which binds a domain common to $VEGF_{xxx}$ and $VEGF_{xxx}b$. For coupling the label to the second antibody, streptavidin is used. This ELISA is specific to $VEGF_{xxx}b$ in the sample and is not cross-reactive with any $VEGF_{xxx}$ present. ELISA and related assay methods can be carried out in a variety of physical formats. For example, in sample vessels such as multiwell plates and tubes, and in particle-based (for example bead-based) formats.

Reference $VEGF_{xxx}b$ Level

The reference $VEGF_{xxx}b$ level is generally calculated from gestational age matched mean values obtained from a population of normotensive pregnant females, namely females who completed their pregnancies without pre-eclampsia.

The data presented below shows that different assay methods for quantitating the $VEGF_{xxx}b$ level in a sample can yield different $VEGF_{xxx}b$ levels, probably due to different patterns of binding by the different antibodies or binding molecules used. Therefore, whenever possible the assay method for obtaining the detected $VEGF_{xxx}b$ level in the subject should correspond quantitatively to the assay method for obtaining the reference $VEGF_{xxx}b$ level. The correspondence can be readily cross-checked by assays performed on known standard solutions of $VEGF_{xxx}b$, in cases where this needs to be verified.

FIG. 1 shows that a suitable reference level in human serum for use in the method for detecting a risk of developing pre-eclampsia will be between about 0.5 and about 3.5 ng/ml, for example between about 2 and about 3 ng/ml, when the $VEGF_{xxx}b$ is $VEGF_{165}b$ sampled at up to about 24 weeks of gestation, such as up to about 12 weeks of gestation, as measured by a sandwich ELISA using two monoclonal antibodies raised against the human VEGF peptide sequence, for example ELISA assay 45-VEGFH-0111, available from Alpco Diagnostics, Salem, N.H. (www.alpco.com/index.asp).

The same data show that a suitable reference level in human serum or plasma for use in the method for detecting a risk of developing severe pre-eclampsia, and particularly severe early-onset pre-eclampsia, will be between about 0.5 and about 2 ng/ml, for example between about 0.5 and about 1.5 ng/ml, when the $VEGF_{xxx}b$ is $VEGF_{165}b$ sampled at up to about 24 weeks of gestation, such as up to about 12 weeks of gestation, as measured by a sandwich ELISA in which the immobilised antibody is a monoclonal antibody specific for a C terminal epitope of $VEGF_{165}b$ (e.g., MAB3045, clone 56/1; R & D Systems) and the label (e.g., the enzyme horseradish peroxidise) is bound to the immobilised antigen via a polyclonal anti-(human VEGF) antibody (e.g., BAF293; R& D Systems) which binds a domain common to $VEGF_{xxx}$ and $VEGF_{xxx}b$.

Generally speaking, where there is a statistically significant difference between the determined $VEGF_{xxx}b$ level and the normal level, there is a significant risk that the tested individual will develop pre-eclampsia. The reference level is to be chosen to represent that statistical significance where the detected $VEGF_{xxx}b$ level is below the reference level.

Alternative reference levels can be selected according to the requirements of the assay. For example, in a longitudinal study of a patient the reference level may be a level of the same patient at a different time point.

Risk Estimation

In principle the risk of a pregnant individual developing pre-eclampsia, and the risk of consequential maternal or fetal complications, can be estimated by analysis of the detected $VEGF_{xxx}b$ levels and the age matched data collected in a patient population study, and applying known statistical analysis methods to estimate the risk, taking into account such additional risk factors as genetic pre-disposition and the sensitivity and specificity of the assay.

In one embodiment, the risk of a pregnant individual developing pre-eclampsia, and the risk of consequential maternal or fetal complications, is estimated from the detected $VEGF_{xxx}b$ level and the age matched population data, taking into account such additional risk factors as genetic pre-disposition.

According to another embodiment, there is provided a method of testing a female mammalian subject for risk of developing pre-eclampsia or a complication linked thereto, the method comprising genotyping the subject to determine a risk of underexpressing $VEGF_{xxx}b$ relative to normal $VEGF_{xxx}b$ level before about 24 weeks of gestation in pregnancy. The genotyping data thereby obtained can be included in the risk estimation. The genotyping can, for example, determine the genetic pre-disposition of the subject to under-expressing $VEGF_{xxx}b$ as a result of particular patterns of splicing during processing of the VEGF pre-mRNA transcribed from the C terminal exon 8 of the VEGF-A gene, as discussed in more detail in WO2008/110777.

The data presented herein (FIG. 6) show that the detection method according to the present description has a relatively high sensitivity (high proportion of true positive predictions of pre-eclampsia and low proportion of false positive predictions of pre-eclampsia) and a relatively high specificity (high proportion of true negative predictions of (no) pre-eclampsia and low proportion of false negative predictions of (no) pre-eclampsia). Therefore, the methods according to the present invention provide a useful and accurate predictor of pre-eclampsia risk that will provide the potential for quantitative risk estimation by statistical analysis.

The method of detecting a risk of a pregnant female mammal developing pre-eclampsia or a complication linked thereto, or of a fetus of the pregnant female mammal developing a fetal or neonatal deficiency linked to maternal pre-eclampsia, according to the present invention, can be used in association with other such methods. Examples of other such methods can include risk detection methods which target (e.g., monitor maternal levels of) one or more other biomarkers indicative of a risk of pre-eclampsia and complications linked thereto. The detection of the level of a $VEGF_{xxx}b$ in a sample from the pregnant female mammal can be performed simultaneously or sequentially (in any desired order) with the detection of the level of the one or more other biomarkers. The detections can be performed on the same or different samples, or in vivo without removing a sample from the mother's body.

$VEGF_{xxx}b$ Level for Treatment

According to another aspect of the present invention, there is provided a method of reducing the risk of a female mammal developing pre-eclampsia or a complication linked thereto, or of a fetus of the female mammal developing a fetal or neonatal deficiency linked to maternal pre-eclampsia, comprising increasing the level of a $VEGF_{xxx}b$ in the female mammal before about the end of the second trimester of the mammal's pregnancy to a level at which the risk of the pregnant female mammal developing pre-eclampsia or a complication linked thereto or of the fetus developing the fetal or neonatal deficiency linked to maternal pre-eclampsia is lowered.

For this purpose, the desirable raised $VEGF_{xxx}b$ level will typically be above the corresponding reference level for the detection of a risk of development of pre-eclampsia and the associated risks according to the first aspect of the invention. For example, the desirable raised level will be at least 20%, for example at least 30% above the corresponding reference level for the first aspect of the invention. In some instances, the desirable raised level will be at least about 75%, for example between about 75% and about 100%, of the gestational age matched mean $VEGF_{xxx}b$ levels for the normotensive population.

For quantitating the $VEGF_{xxx}b$ levels of the subject, quantitatively analogous assay methods should be used, as between the data obtaining the gestational age matched mean $VEGF_{xxx}b$ levels for the normotensive population, any data establishing a risk of a subject developing pre-eclampsia, and the data monitoring the increased $VEGF_{xxx}b$ level obtained as a result of treatment according to this aspect of the invention.

FIG. 1 of the accompanying drawings shows that a suitable level in human serum for reducing a risk of developing pre-eclampsia will be at least about 2 ng/ml, for example between about 2.0 and about 4.5 ng/ml, for example between about 2.5 and about 4 ng/ml, when the $VEGF_{xxx}b$ is $VEGF_{165}b$ sampled at up to about 24 weeks of gestation, such as up to about 12 weeks of gestation, as measured by a sandwich ELISA in which the immobilised antibody is a monoclonal antibody specific for a C terminal epitope of $VEGF_{165}b$ (e.g., MAB3045, clone 56/1; R & D Systems) and the label (e.g., the enzyme horseradish peroxidise) is bound to the immobilised antigen via a polyclonal anti-(human VEGF) antibody (e.g., BAF293; R & D Systems) which binds a domain common to $VEGF_{xxx}$ and $VEGF_{xxx}b$.

Test Kit

The kit, for use in determining an increased risk to a pregnant female mammal of pre-eclampsia or a complication linked thereto or to the fetus of the pregnant female mammal of developing a fetal or neonatal deficiency linked to maternal pre-eclampsia, comprises one or more reagent for detection of the level of a $VEGF_{xxx}b$ in a sample from the pregnant female mammal. The kit can further comprise instructions for use of the reagent(s). The reagents can comprise antibodies against the VEGF$_{xxx}$b, or receptors or binding molecules to the VEGF$_{xxx}$b, or combinations thereof. Any of these antibodies, receptors or binding molecules can be labelled with detectable markers (e.g., fluorescent or radioactive or enzyme markers) to allow detection, or can themselves be detectable with labelled secondary antibodies or binding molecules or enzymes. Any of the antibodies, receptors or binding molecules can be either in solution or affixed to a solid support in conventional manner. The kit can further comprise means for taking a sample from a subject mammal, such as, for example, swabs, syringes and the like.

The kit can be adapted for use with electronic apparatus to detect the markers (labels) quantitatively. The apparatus can suitably comprise stations for holding containers in which the sample and/or reagents and/or standard mixtures for quantitation are retained. Such apparatus are conventional in the assay methods and further description is not required here.

VEGF$_{xxx}$b Active Agent

The term "VEGF$_{xxx}$b active agent" encompasses VEGF$_{xxx}$b protein materials (including, but not limited to, full protein and anti-angiogenic fragments thereof) and agents which promote the presence or endogenous expression of VEGF$_{xxx}$b relative to the normal or untreated subject, optionally relative to VEGF$_{xxx}$, in vivo or in vitro.

The VEGF$_{xxx}$b active agent used in the presently described methods can be prepared by any suitable means.

The use of agents, acting on cells to promote the endogenous expression of VEGF$_{xxx}$b in preference (i.e. relative) to VEGF$_{xxx}$ in the cells, is one possible way of preparing the VEGF$_{xxx}$b for use in the presently described methods. For further details of the agents, see WO2008/110777.

The term "VEGF$_{xxx}$b active agent" thus includes within its scope an expression vector system which causes the expression of the VEGF$_{xxx}$b in a host organism. This can be the subject to be treated or another organism suitable to the subject to be treated. Such an expression vector system suitably comprises a promoter nucleotide sequence operably associated a nucleotide sequence coding for the VEGF$_{xxxb}$, whereby the VEGF$_{xxx}$b can be expressed in the host organism under suitable conditions of transfection and incubation. Further details are provided below in the section headed "Gene Therapy".

The term "VEGF$_{xxx}$b active agent" thus also includes within its scope an inhibition system for VEGF$_{xxx}$ in a host organism, suitably the subject to be treated, whereby the proportion of active VEGF$_{xxx}$b to VEGF$_{xxx}$ is increased in the host organism or particular tissues thereof. Such an inhibition system can, for example, comprise a specific anti-VEGF$_{xxx}$ antibody, for example a monoclonal or polyclonal specific anti-VEGF$_{xxx}$ antibody [15, 16, 25]. The inhibition system can alternatively comprise an expression vector system which causes the expression of an inhibition system for VEGF$_{xxx}$ in a host organism. Such an expression vector system suitably comprises a promoter nucleotide sequence operably or functionally associated a nucleotide sequence coding for a protein inhibition system for VEGF$_{xxx}$, such as a specific anti-VEGF$_{xxx}$ antibody, whereby the protein inhibition system for VEGF$_{xxx}$ can be expressed in the host organism under suitable conditions of transfection and incubation.

More than one type of VEGF$_{xxx}$b active agent, and/or more than one embodiment of any particular type of VEGF$_{xxx}$b active agent, can be used simultaneously or sequentially if desired.

VEGF$_{xxx}$b Active Agents which Selectively Promote the Expression of VEGF$_{xxx}$b in Preference (i.e. Relative) to VEGF$_{xxx}$ in Cells of a Subject or In Vitro Such agents are described in the passage from page 6, line 22 to page 8, line 9 of WO-A-2008/110777, and elaborated in the remainder of WO-A-2008/110777 to the extent that favouring of DSS splicing over PSS splicing is concerned. Please refer to these passages of WO-A-2008/110777 for the discussion.

In particular, there can be mentioned Transforming Growth Factor (TGF)-b1, TGF-b R1, SRPK1 specific inhibitors (for example, SRPIN 340), T-cell intercellular antigen-1 (TIA-1), MKK3/MKK6-activatable MAP kinases (for example, p38 MAPK), Cdc20-like (Clk) family kinases Clk1/sty, Clk2, Clk3 and Clk4, the SR splicing factor SRp55, their in vivo activators, upregulators and potentiators, functionally active analogues and functionally active fragments of any of the foregoing, modified forms of any of the foregoing having a secondary functionality useful for control of their primary activity or the effects thereof, expression vector systems for expressing any of the foregoing agents in vivo, transcription/translation blocking agents which bind to the PSS of exon 8a of the pre-mRNA and/or at the region of the pre-mRNA to which a splicing regulatory protein binds, to inhibit proximal splicing (for example, morpholinos or other synthetic blocking agents, peptide conjugates, RNA binding proteins, RNA interference (RNAi) poly- and oligonucleotide blocking agents (for example dsRNA, microRNA (miRNA), siRNA), peptide nucleic acid (PNA), protein kinase C (PKC) inhibitors (for example, bisindolyl maleimide (BIM) and other mechanistically analogous PKC inhibitors, particularly inhibitors which bind at the PKC catalytic domain), or any combination thereof.

Such an expression vector system suitably comprises a promoter nucleotide sequence operably associated a nucleotide sequence coding for the agent promoting expression of VEGF$_{xxx}$b in preference to VEGF$_{xxx}$, whereby the agent promoting expression of VEGF$_{xxx}$b in preference to VEGF$_{xxx}$ can be expressed in a host organism, suitably the subject to be treated, under suitable conditions of transfection and incubation. Further details are provided below in the section headed "Gene Therapy".

Compositions and Administration

For performing an aspect of the present invention, an active agent can be administered in the form of a composition comprising the active agent and any suitable additional component. The composition can, for example, be a pharmaceutical composition (medicament).

The active agent according to the present invention can be administered in the form of a composition comprising the active agent and any suitable additional component. The composition can, for example, be a pharmaceutical composition (medicament), suitably for parenteral administration (e.g., injection, implantation or infusion) or suitable for oral administration.

A composition can further comprise one or more additional active agent known to alleviate or prevent pre-eclampsia and complications linked to pre-eclampsia. A composition can be administered in association with (e.g., simultaneously or sequentially with) one or more additional compositions containing one or more additional active agent known to alleviate or prevent pre-eclampsia and complications linked to pre-eclampsia. Such additional active agents include, for example, aspirin, e.g., orally administered aspirin, for reducing incidence of pre-eclampsia.

The term "pharmaceutical composition" or "medicament" in the context of this invention means a composition comprising an active agent and comprising additionally one or more pharmaceutically acceptable carriers. The composition can further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions can take the form, for example, of tablets, dragees, powders, elixirs, syrups, liquid preparations including suspensions, sprays, inhalants, tablets, lozenges, emulsions, solutions, cachets, granules, capsules and suppositories, as well as liquid preparations for injections, including liposome preparations. Techniques and formulations generally can be found in Remington, The Science and Practice of Pharmacy, Mack Publishing Co., Easton, Pa., latest edition.

Liquid form preparations include solutions, suspensions, and emulsions. As an example can be mentioned water or water-propylene glycol solutions for parenteral injection. Liquid preparations can also be formulated in solution in aqueous polyethylene glycol solution.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternatively, sufficient solid can be provided so that after conversion to liquid form, multiple individual liquid doses can be obtained by measuring predetermined volumes of the liquid form preparation as with a syringe, teaspoon, or other volumetric container or apparatus. The solid form preparations intended to be converted to liquid form can contain, in addition to the active material, flavourings, colourants, stabilizers, buffers, artificial and natural sweeteners, dispersants, thickeners, solubilising agents, and the like. The liquid utilized for preparing the liquid form preparation can be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

The dosages can be varied depending upon the requirements of the patient, the severity of the condition being treated, and the compound being employed. Determination of the proper dosage for a particular situation is within the skill of the art. Generally, treatment is initiated with the smaller dosages which are less than the optimum dose of the compound. Thereafter the dosage is increased by small increments until the optimum effect under the circumstances is reached. For convenience, the total daily dosage can be divided and administered in portions during the day if desired.

Gene Therapy

The third aspect of the present invention can be practiced using gene therapy. Gene therapy techniques are generally known in this art, and the present invention can suitably be put into practice in these generally known ways. The following discussion provides further outline explanation.

The gene therapies are broadly classified into two categories, i.e., in vivo and in vitro therapies. The in vivo gene therapy comprises introducing a therapeutic gene directly into the body, and the in vitro gene therapy comprises culturing a target cell in vitro, introducing a gene into the cell, and then introducing the genetically modified cell into the body.

The gene transfer technologies are broadly divided into a viral vector-based transfer method using virus as a carrier, a non-viral delivery method using synthetic phospholipid or synthetic cationic polymer, and a physical method, such as electroporation or introducing a gene by applying temporary electrical stimulation to a cell membrane.

Among the gene transfer technologies, the viral vector-based transfer method is considered to be preferable for the gene therapy because the transfer of a genetic factor can be efficiently made with a vector with the loss of a portion or whole of replicative ability, which has a gene substituted a therapeutic gene. Examples of virus used as the virus carrier or vector include RNA virus vectors (retrovirus vectors, lentivirus vector, etc.), and DNA virus vectors (adenovirus vectors, adeno-associated virus vectors, etc.). In addition, its examples include herpes simplex viral vectors, alpha viral vectors, etc. Among them, retrovirus and adenovirus vectors are particularly actively studied.

The characteristics of retrovirus acting to integrate into the genome of host cells are that it is harmless to the human body, but can inhibit the function of normal cells upon integration. Also, it infects various cells, proliferates fast, can receive about 1-7 kb of foreign genes, and is capable of producing replication-deficient virus. However, it has disadvantages in that it is hard to infect cells after mitosis, it is difficult to transfer a gene in vivo, and the somatic cell tissue is needed to proliferate always in vitro. In addition, since it can be integrated into a proto-oncogene, it has the risk of mutation and can cause cell necrosis.

Meanwhile, adenovirus has various advantages for use as a cloning vector; it has moderate size, can be replicated within a cell nucleus, and is clinically nontoxic. Also, it is stable even when inserted with a foreign gene, and does not cause the rearrangement or loss of genes, can transform eucaryotes, and is stably expressed at a high level even when it is integrated into the chromosome of host cells. Good host cells for adenovirus are cells of causing human hematosis, lymphoma and myeloma. However, these cells are difficult to proliferate because they are linear DNAs. Also, it is not easy infected virus to be recovered, and they have low virus infection rate. Also, the expression of a transferred gene is the highest after 1-2 weeks, and in some cells, the expression is kept only for about 3-4 weeks. In addition, these have the problem of high immune antigenicity.

Adeno-associated virus (AAV) can overcome the above-described problems and at the same time, has many advantages for use as a gene therapeutic agent and thus is recently considered to be preferable. AAV, which is single-strand provirus, requires an assistant virus for replication, and the AAV genome is 4,680 by in size and can be inserted into any site of chromosome 19 of infected cells. A trans-gene is inserted into plasmid DNA linked with 145 by of each of two inverted terminal repeat sequence (ITR) and a signal sequence. This gene is transfected with another plasmid DNA expressing AAV rep and cap genes, and adenovirus is added as an assistant virus. AAV has advantages in that the range of its host cells to be transferred with a gene is wide, immune side effects due to repeated administration are little, and the gene expression time is long. Furthermore, it is stable even when the AAV genome is integrated into the chromosome of a host cell, and it does not cause the modification or rearrangement of gene expression in host cells. Since an AAV vector containing a CFTR gene was approved by NIH for the treatment of cystic fibrosis in 1994, it has been used for the clinical treatment of various diseases. An AAV vector containing a factor IXgene, which is a blood coagulation factor, is used for the treatment of hemophilia B, and the development of a therapeutic agent for hemophilia A with the AAV vector is currently being conducted. Also, AAV vectors containing various kinds of anticancer genes were certified for use as tumor vaccines.

Gene therapy, which is a method of treating diseases by gene transfer and expression, is used to adjust a certain gene, unlike the drug therapy. The ultimate purpose of the gene therapy is to obtain useful therapeutic effects by genetically modifying a living gene. The gene therapy has various advantages, such as the accurate transfer of a genetic factor into a disease site, the complete decomposition of the genetic factor in vivo, the absence of toxicity and immune antigenicity, and the long-term stable expression of the genetic factor and thus is spotlighted in connection with the present invention as a potentially suitable route of treatment.

The host cell for the gene therapy, to which the gene therapy is targeted, can be a cell of a type that normally expressed the $VEGF_{xxx}b$.

In general, reference herein to the presence of one of a specified group of compounds, for example $VEGF_{xxx}b$, includes within its scope the presence of a mixture of two or more of such compounds.

BRIEF DESCRIPTION OF THE DRAWINGS

The invention will be described in greater detail below, without limitation and purely by way of illustration, with reference to the accompanying drawings, in which.

Figure 1:
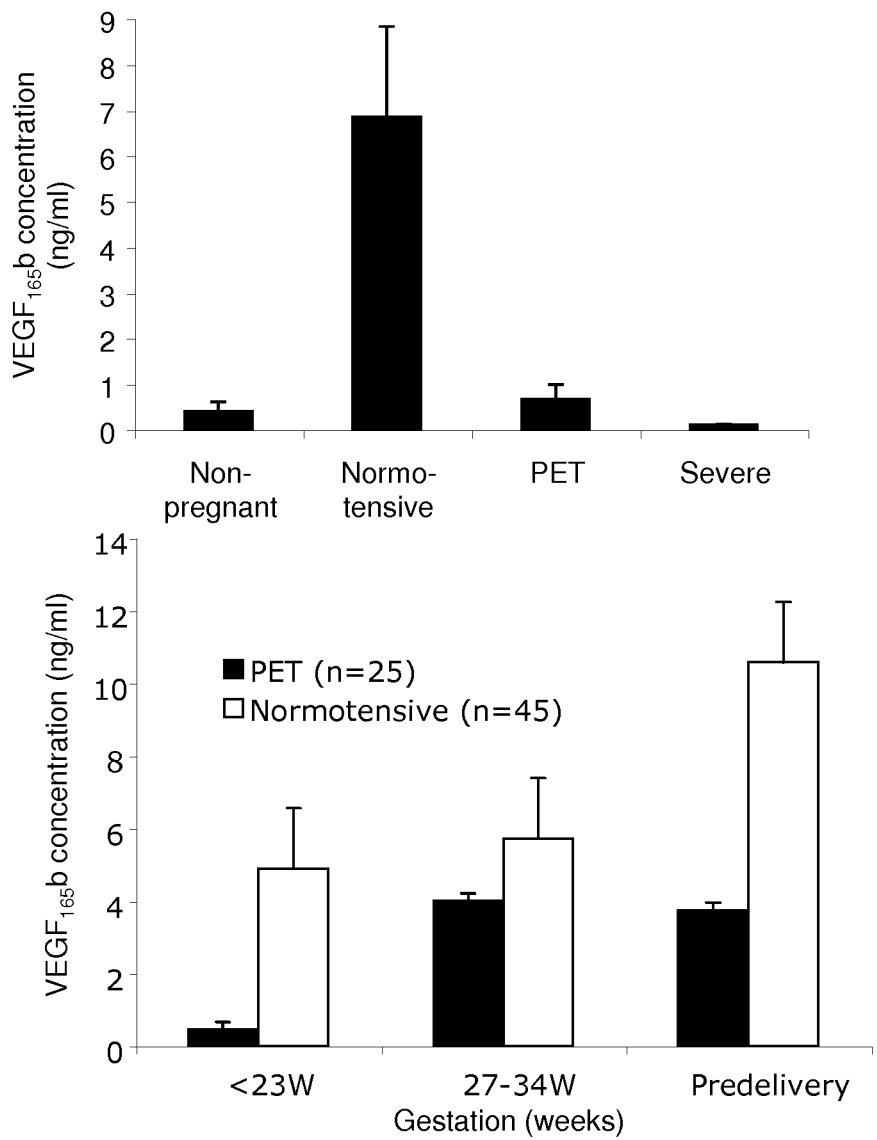
FIG. 1 shows mean $VEGF_{165}b$ levels in (upper panel) non-pregnant women's plasma (denoted "non-pregnant" on the horizontal axis), normotensive pregnant maternal plasma at 12 weeks gestation (denoted "normotensive" on the horizontal axis), non-severe preclamptic (PET) maternal plasma at 12 weeks gestation (denoted "PET" on the horizontal axis) and severe early-onset pre-eclampsia maternal plasma at 12 weeks gestation (denoted "Severe" on the horizontal axis); and (lower panel) pregnant maternal plasma of women with severe/early onset pre-eclampsia (left hand bars of each bar pair, shaded black and denoted "PET (n=25)") and of normotensive pregnant women (right hand bars of each bar pair, shaded white and denoted "Normotensive (n=45)") at up to 23 weeks of gestation (denoted "<23 W" on the horizontal axis), 27 to 34 weeks of gestation (denoted "27-34 W" on the horizontal axis) and immediately pre-delivery (denoted "Pre-delivery" on the horizontal axis)

When referring to the drawings, the following figure legends are helpful:

FIG. 1: Measurement of $VEGF_{165}b$ levels in human plasma (Upper panel) At 12 weeks of gestation, $VEGF_{165}b$ was increased in plasma from pregnant women who went on to have normotensive pregnancies (n=45) compared with non-pregnant women. This was not the case in patients who subsequently developed severe, early onset and non severe pre-eclampsia (n=25); P=0.0003, as determined using a one-way ANOVA and Kruskal-Wallis test). Subgroup analysis of severe/early-onset pre-eclampsia patients (n=9) compared with normotensive subjects also showed that $VEGF_{165}b$ is significantly lowered (P=0.008, as determined using a Mann-Whitney U test). (Lower panel) $VEGF_{165}b$ levels in both pre-eclamptic patients and normotensive subjects was increased in the third trimester (P=0.0012, as determined using a Mann-Whitney U test). Values are means±S.E.M. PET=pre-eclampsia.

Figure 2:
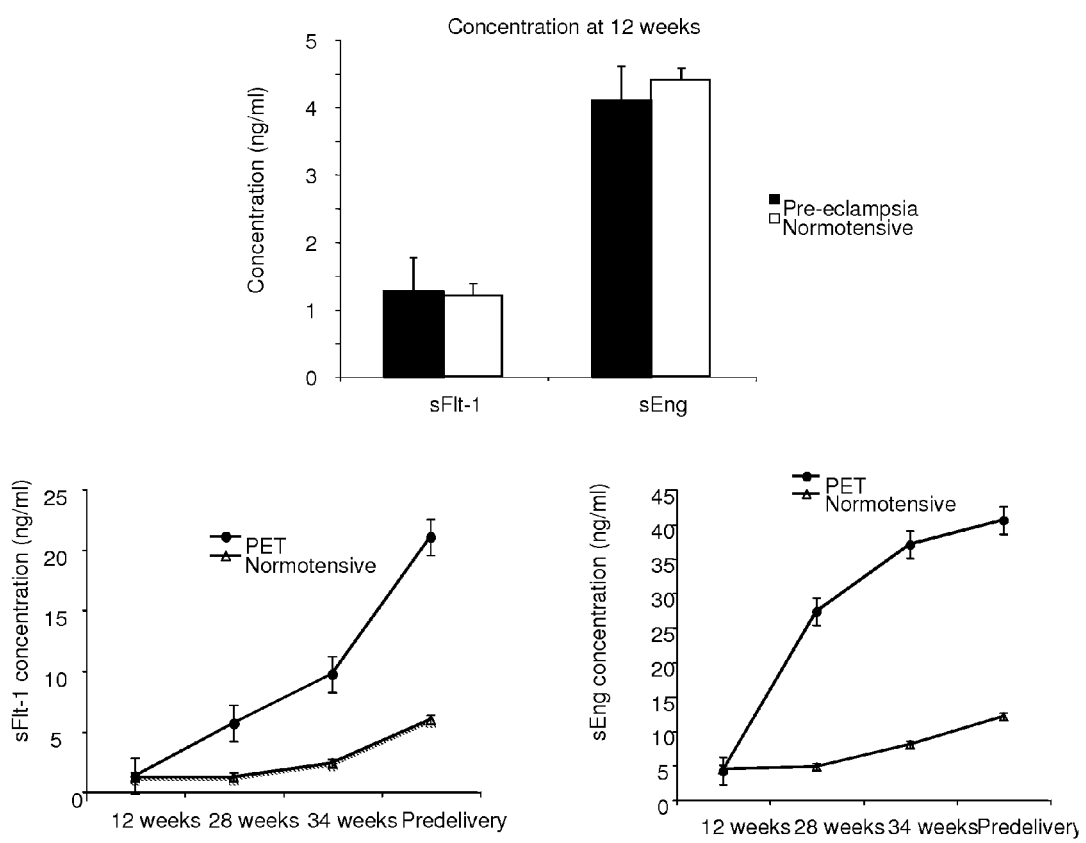
FIG. 2 shows (upper panel) mean sFlt-1 and soluble endoglin (sEng) levels in pregnant maternal plasma at 12 weeks of gestation in subjects who did (left hand bars of each bar pair, shaded black and denoted "Pre-eclampsia") or did not (right hand bars of each bar pair, white and denoted "Normotensive") go on to develop pre-eclampsia; (bottom left panel) mean sFlt-1 levels at 12, 28, 34 weeks of gestation and at term ("Pre-delivery") in subjects who did (upper curve, denoted "PET") or did not (lower curve, denoted "Normotensive") develop pre-eclampsia; and (bottom right panel) mean sEng levels at 12, 28, 34 weeks of gestation and at term ("Pre-delivery") in subjects who did (upper curve, denoted "PET") or did not (lower curve, denoted "Normotensive") develop pre-eclampsia.

FIG. 2: First trimester sFlt-1 and sEng do not predict an increased risk of pre-eclampsia. (Upper panel) At 12 weeks of gestation, healthy subjects and subjects who later developed pre-eclampsia had similar levels of both sFlt-1 and sEng. Neither plasma marker was able to predict pre-eclampsia at 12 weeks of gestation. Pre-eclampsia was associated with up-regulation of maternal plasma levels of sFlt-1 (bottom left-hand panel) and sEng (bottom right-hand panel) relative to first trimester levels. In normotensive pregnancies, plasma levels of both molecules increased with advancing gestational age by 2.8-fold (sEng) and 5.3-fold (sFlt-1). P<0.001, as determined using a Mann-Whitney U Test. Values are means±S.E.M. PET=pre-eclampsia.

Figure 3:
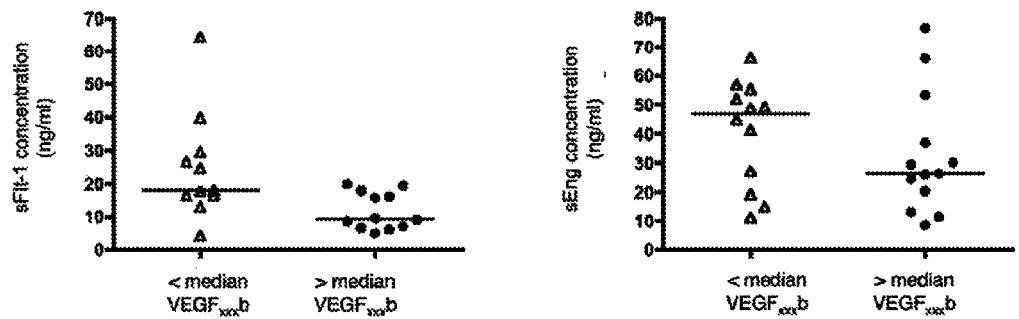
FIG. 3 shows (left hand panel) the relationship between low $VEGF_{165}b$ plasma levels in the first trimester and sFlt-1 levels at onset of pre-eclampsia (left hand group of subject data points, indicated by triangles) and between high $VEGF_{165}b$ plasma levels in the first trimester and sFlt-1 levels at onset of pre-eclampsia (right hand group of subject data points, indicated by solid circles); and (right hand panel) the relationship between low $VEGF_{165}b$ plasma levels in the first trimester and sEng levels at onset of pre-eclampsia (left hand group of subject data points, indicated by triangles) and between high $VEGF_{165}b$ plasma levels in the first trimester and sEng levels at onset of pre-eclampsia (right hand group of subject data points, indicated by solid circles)

FIG. 3: Lack of up-regulation of $VEGF_{165}b$ in the first trimester is able to predict the elevated sFlt-1 concentration occurring with the onset of pre-eclampsia but not sEng. For sFLt-1, P=0.028, as determined using a Mann-Whitney U test. However, first trimester $VEGF_{165}b$ does not correlate with sEng concentration at pre-eclampsia diagnosis.

Figure 4:
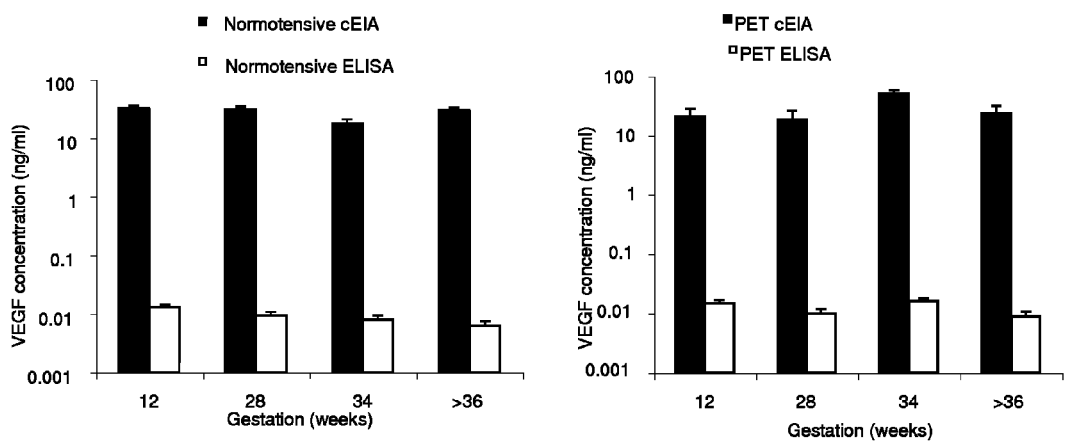
FIG. 4 shows (left hand panel) total plasma VEGF measured at 12, 28, 34 and more than 36 weeks of gestation by cEIA (left hand bars of each bar pair, shaded black and denoted "Normotensive cEIA) or ELISA (right hand bars of each bar pair, white and denoted "Normotensive ELISA") in subjects who did not go on to develop pre-eclampsia; and (right hand panel) total plasma VEGF measured at 12, 28, 34 and more than 36 weeks of gestation by cEIA (left hand bars of each bar pair, shaded black and denoted "PET cEIA) or ELISA (right hand bars of each bar pair, white and denoted "PET ELISA") in subjects who did go on to develop pre-eclampsia.

FIG. 4: Total VEGF was quantified both by EIA (left hand bars of each bar pair; shown in black) and ELISA (right-hand bar of each bar pair, shown in white) in maternal plasma from normotensive and pre-eclamptic pregnancies (n=10). Detectable levels of VEGF were 2500-fold lower when measured by ELISA compared to EIA, (P<0.0001 as determined using a Mann-Whitney U test). PET=pre-eclampsia. Values are means±S.E.M.

Figure 5:
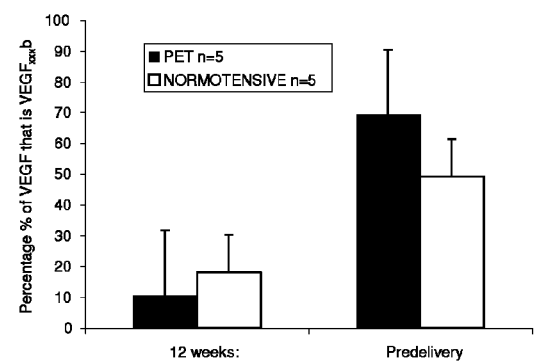
FIG. 5 shows the proportion of total plasma VEGF that is $VEGF_{165}b$ measured at 12 weeks (left hand pair of pars) and pre-delivery (right hand pair of bars) in subjects who did (left hand bars of each bar pair, shaded black and denoted "PET, n=5") or did not (right hand bars of each bar pair, white and denoted "Normotensive n=5") go on to develop pre-eclampsia.

FIG. 5: Increase in total VEGF levels observed during pregnancy are primarily due to increased VEGF$_{165}$b. At 12 weeks, only a small proportion of total VEGF (10-18%) was VEGF$_{165}$b (n=10). In contrast, at term approximately 50% of the VEGF was VEGF$_{165}$b in normotensive subjects, whereas in pre-eclampsia 70% of total VEGF was VEGF$_{165}$b. Values are means±S.E.M. PET=pre-eclampsia.

Figure 6:
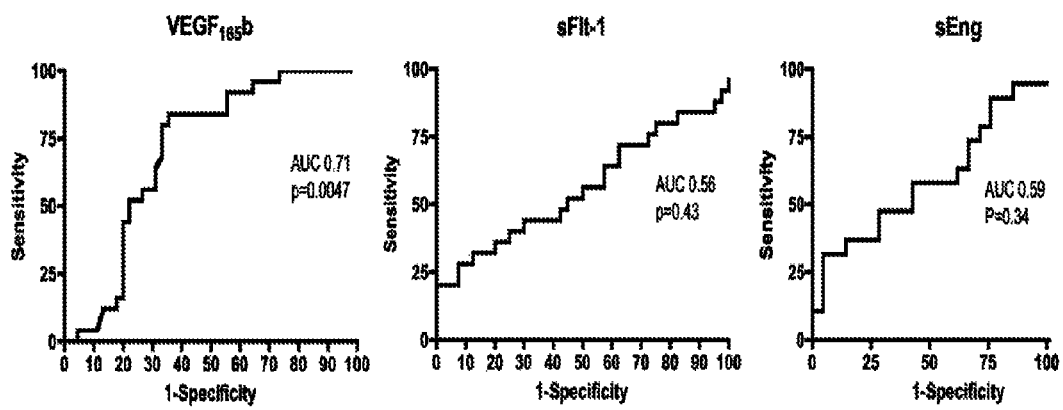
FIG. 6 shows ROC curves for first trimester $VEGF_{165}b$ (left hand panel), sFlt-1 (middle panel) and sEng (right hand panel).

FIG. 6: Receiver-operating characteristic (ROC) curves for first trimester VEGF$_{165}$b, sFlt-1 and sEng in the prediction of pre-eclampsia. Area under the curve (AUC) was highest for VEGF$_{165}$b, at 0.71 [P=0.0047 compared with random (0.5)]. AUC for sEng and sFlt-1 were 0.59 (P=0.34) and 0.56 (P=0.43) respectively, and were not different from random (0.5).

Example

Pregnant subjects were recruited from St Michael's Maternity Hospital, Bristol, UK, between June 2006 and December 2007. 18 non-pregnant females aged between 20 and 39 years were recruited from the University of Bristol, UK. The protocol for this study was granted ethical approval by Central and South Bristol Research Ethics Committee. 50 subjects were recruited from routine antenatal clinics in the first trimester of pregnancy. Subjects were aged between 17 and 42 years.

Blood was taken from subjects for VEGF$_{165}$b quantification at recruitment, and at a further three times at 28, 34 and 37 weeks of gestation.

Pre-eclampsia was defined as blood pressure (BP)≧140/90 mmHg on two or more occasions measured 6 hours apart and ≧300 mg of proteinuria/24 hours, in the absence of a urinary tract infection, occurring after 20 weeks of gestation. The expression "weeks of gestation" used herein refers to the number of weeks since the mother's last menstruation.

Five patients who later developed pre-eclampsia had further blood taken at disease diagnosis.

Following venepuncture, blood was immediately centrifuged at 4000 rpm (179 g) for 10 minutes at 5° C., the supernatant was removed and stored at −80° C. until protein quantification.

Subjects also received fetal growth ultrasound scans at 28, 34 and 37 weeks of gestation to screen for intra-uterine growth restriction secondary to pre-eclampsia.

During the study period, a further 20 patients who developed pre-eclampsia in the third trimester were recruited into the study at disease diagnosis, and received fetal growth scans at the point of recruitment into the study. In these cases, plasma from their first trimesters was obtained from aliquots of frozen plasma stored under the same standard blood storage conditions by the hospital's virology department.

Sample size was calculated to observe an 80% change in mean VEGF$_{165}$b levels at P<0.05 with a power of >90% given a standard deviation (S.D.) equivalent to the mean (calculated using G Power).

Anti-VEGF$_{xxx}$b antibody (MAB3045, clone 56/1, R&D Systems) was coated overnight onto the surface of a sterile Immulon-2HB 96-well plate at a concentration of 200 µg/ml. This antibody recognises an epitope within a nine amino-acid sequence at the C terminus of human VEGF$_{165}$b. The plate was washed three times with 100 µl/well of phosphate buffered saline (PBS)/0.05% Tween 20. The plate was blocked for 12 hours with Superblock (250 µl/well; Pierce 37515). Serial dilutions of recombinant VEGF$_{165}$b standards (R&D Systems) diluted in phosphate buffered saline/bovine serum albumin (PBS/BSA) up to a concentration of 16 ng/ml were then added to the wells in triplicate (200 µl/well). Plasma samples were also added in triplicate (200 µl/well). Plates were then incubated at room temperature (22-24° C.) with shaking for 2 hours and then washed as above. Biotinylated anti-(human VEGF) affinity-purified polyclonal antibody (50 ng/ml; BAF293, R&D Systems), as a detection agent, was added (200 µl/well) and incubated at room temperature with shaking for 2 hours with the plate protected from light. Following a further wash, 100 µl HRP (horseradish peroxidase)-streptavidin diluted 1:200 in PBS was added for 20 minutes protected from light, and then substrates A and B (100 µl/well) were added following washing. After 25 minutes the colour change was stopped on addition of 1M H$_2$SO$_4$ (50 µl/well), and the plates were read immediately at a wavelength of 450 nm using a plate photospectrometer (Dynex Technologies). Revelation Quicklink 4.25 software was used to construct a standard curve from mean absorbance values of VEGF$_{165}$b standards, which enabled estimation of the VEGF$_{165}$b concentration in plasma samples. VEGF$_{165}$b sample concentrations were quantified at multiple different concentrations in triplicate to ensure that values were in the range of the ELISA. Values were expressed as means±S.E.M.

This sandwich ELISA measures total circulating VEGF$_{165}$b. It has been shown not to detect VEGF$_{165}$ and sFlt-1 is known not to interfere due to the use of antibodies against the VEGF$_{165}$b molecule with epitopes at different parts of the molecule [Reference 15]. The coefficients of variation (CVs) of this assay in quantifying VEGF$_{xxx}$b was 17% for within-subject variation (samples taken at least a week apart), and 7% for within-sample variation, whereas between-sample CV was >200%, indicating consistency of assay, and significant variation amongst the population.

VEGF$_{165}$b concentration in maternal plasma was quantified at 8-12, 28, 34 and 37 weeks of gestation in 45 normotensive subjects and four subjects recruited in the first trimester who later developed pre-eclampsia in the third trimester. The VEGF$_{165}$b concentration was also quantified in 21 pre-eclamptic patients at 12 weeks of gestation and again in the third trimester at disease diagnosis. A similar version of this ELISA is available as a DuoSet Kit from R&D Systems.

Endoglin and sFlt-1 ELISAs

ELISAs for sEng and sFlt-1 were carried out on maternal plasma samples using commercial ELISA kits from R&D Systems (DNDG00 and DVR100B respectively), according to the manufacturer's instructions. Values are expressed as means±S.E.M.

Total VEGF ELISA and EIA

Total circulating VEGF was quantified by commercial ELISA (45-VEGFH-0111; Alpco Diagnostics) and by competitive enzyme immunoassay (cEIA) (QIA69; Calbiochem). The EIA measures both bound and free forms of VEGF.

We had access to only a single 96 well cEIA for total VEGF quantification. For this reason total VEGF quantification was possible in only ten patients. For each plasma sample, VEGF concentration was determined both by ELISA and EIA. Values are expressed as means±S.E.M.

During the study period, 100 patients were recruited: 25 patients had pre-eclampsia, and 45 remained normotensive. Of the 30 recruits who were excluded from the study, five developed pregnancy-induced hypertension, one developed idiopathic fetal growth restriction, nine chose not to attend follow up appointments due to social reasons, two experienced intra-uterine deaths at 21 and 28 weeks of gestation, three experienced pre-term labour in the absence of pre-eclampsia, and ten with pre-eclampsia had no first trimester blood sample available.

The mean maternal age within the normotensive (n=45) and pre-eclamptic (n=25) groups were 30±0.8 and 30±1.3 years respectively (Table 1).

TABLE 1

Clinical characteristics of the study participants.

| Characteristic | Normotensive (n = 45) | Pre-eclampsia (n = 25) |
|---|---|---|
| Maternal age (years) | 30 ± 0.8 | 30 ± 1.3 |
| Gestational age at diagnosis (weeks) | NA | 34 + 5 ± 0.6 |
| Gestational age at birth (weeks) | 39 + 3 ± 0.17 | 36.3 ± 0.47 |
| Systolic BP (mmHg) | <140 | 151 ± 3.1 |
| Diastolic BP (mmHg) | <90 | 98 ± 1.7 |
| Proteinuria (g/24 hours) | <0.3 | 1.3 ± 0.17 |
| Primiparous (%) | 58 | 52 |
| Birth weight (g) | 3495 ± 481 | 2513 ± 166 |
| Platelet count ($10^9$/l) | 259 ± 10 | 206 ± 17 |
| Creatinine (mmol/l) | 60 ± 1.3 | 79 ± 2.5 |

Values shown are mean ± SEM.
NA = not applicable.

There were no differences in smoking status or ethnicity between the groups. Within the pre-eclampsia group, the mean gestational age at diagnosis was 34+5±0.6 weeks, the mean proteinuria was 1.3±0.17 g/24 hours, and the mean blood pressure was 151/98±3.1/1.7 mmHg (Table 1).

Mean birth weight within the pre-eclamptic and normotensive groups was 2513±166 g and 3495±481 g respectively. Of the 25 pre-eclamptic patients, six developed early-onset pre-eclampsia (<34 weeks gestation) and 12 developed pre-eclampsia between 34 and 37 weeks gestation. The remaining seven patients developed pre-eclampsia at full term. Five of the 25 pre-eclamptic patients developed severe pre-eclampsia [according to the Royal College of Obstetricians and Gynaecologists criteria: systolic BP>169 mmHg or diastolic BP>109 mmHg with proteinuria>1 gram/24 hours; or the occurrence of HELLP (haemolysis, elevated liver enzymes and low platelet) syndrome]. Five of the 25 fetuses born to pre-eclamptic mothers had growth restriction (ultrasonically defined as estimated fetal weight<$10^{th}$ percentile for gestational age with further evidence of placental insufficiency, such as oligohydramnios or abnormal umbilical artery Dopplers [Reference 16]).

Plasma $VEGF_{165}b$ increases in normotensive pregnancy. Plasma $VEGF_{165}b$ concentration from non-pregnant women was 0.4±0.22 ng/ml. In the normotensive group, circulating plasma $VEGF_{165}b$ at 12 weeks of gestation was significantly increased (4.90±1.66 ng/ml, P<0.001, as determined using a Mann-Whitney U test; FIG. 1, upper panel), and remained so throughout pregnancy.

Patients who later develop pre-eclampsia have reduced first trimester $VEGF_{165}b$ levels. At 12 weeks of gestation, the plasma $VEGF_{165}b$ concentration was significantly lower in patients who later developed pre-eclampsia (0.467±0.209 ng/ml) compared with plasma from normotensive pregnancies (FIG. 1, upper panel). When the severe, early onset pre-eclampsia sub group was analysed, a low first trimester $VEGF_{165}b$ concentration was also predictive at 12 weeks (P=0.008, as determined using a Mann-Whitney U test). In contrast, at term there was no significant difference in plasma $VEGF_{165}b$ concentrations between pre-eclamptic (3.75±2.24 ng/ml) and normal pregnancies (10.58±3.74 ng/ml). Thus, pre-eclampsia was associated with an 8±1.8-fold increase in plasma $VEGF_{165}b$ from first trimester to pre-delivery, compared with a 2±0.3-fold increase in normotensive plasma (P<0.0012, as determined using a Mann-Whitney U test).

Patients with a lower than median plasma $VEGF_{165}b$ at 12 weeks, had elevated sFlt-1 and sEng just before delivery. Concentrations of sFlt-1 (1.20±0.07 ng/ml and 1.27±0.18 ng/ml) and sEng (4.4±0.18 and 4.1±0.5 ng/ml) were similar at 12 weeks of gestation in the normotensive and pre-eclamptic groups, respectively (FIG. 2, upper panel). Therefore, at 12 weeks of gestation, neither sFlt-1 nor sEng were able to predict the onset of pre-eclampsia later in the pregnancy (see FIG. 6, middle and right-hand panels). At disease diagnosis, however, both sFlt-1 (FIG. 2, bottom left hand panel) and sEng (FIG. 2, bottom right-hand panel) were significantly up-regulated compared with normotensive subjects (P<0.001, as determined using a Mann-Whitney U test).

$VEGF_{165}b$ predicts sFLT-1 and sEndoglin. The reduced first trimester levels of $VEGF_{165}b$ were able to predict the elevated sFLT-1 which occurred with the onset of pre-eclampsia (FIG. 3, left-hand panel; P=0.028, as determined using a Mann-Whitney U Test). However, $VEGF_{165}b$ concentrations in the first trimester did not correlate with the elevated sEng of pre-eclampsia (FIG. 3, right-hand panel).

Commercial total VEGF ELISAs underestimate total VEGF levels. Total circulating VEGF was quantified in the same plasma samples both by commercial ELISA and EIA. When quantified by ELISA, VEGF concentrations were on average 2500-fold lower than when quantified by EIA (FIG. 4; P<0.0001, as determined using a Mann-Whitney U test).

$VEGF_{165}b$ accounts for the majority of total circulating VEGF in the third trimester in pre-eclamptic pregnancy. In five patients in each group, we were able to quantitate $VEGF_{165}b$ and total VEGF in the same samples.

$VEGF_{165}b$ expression increased in both pre-eclampsia and normotensive pregnancy with increasing gestational age. At 12 weeks of gestation, $VEGF_{165}b$ accounted for 10.5±20% of total plasma VEGF in patients that went on to develop pre-eclampsia, compared with 18.1±10% in control patients (FIG. 5). With the onset of pre-eclampsia, $VEGF_{165}b$ accounted for the majority of total circulating VEGF, comprising 69.3±21% of total plasma VEGF in the patient group and 49±12% in the control group.

$VEGF_{165}b$ levels at 12 weeks predict pre-eclampsia. To determine which of $VEGF_{165}b$, sFlt-1 and sEng are more accurate prognostic factors, receiver operating characteristic (ROC) curves were generated by calculating sensitivity (proportion of times that the test predicts pre-eclampsia) and specificity (proportion of times that the test excluded pre-eclampsia). Thus a high sensitivity value would include all patients, but if not discriminatory would provide a low specificity value (and would include false positives). Thus a non-discriminatory test would give a straight line with a slope of 1 and area under the curve (AUC) of 0.5. A perfect discriminatory test would have an AUC of 1.0. As shown in FIG. 6 (left-hand panel), $VEGF_{165}b$ levels have an AUC significantly greater than 0.5, in contrast with sFlt-1 (FIG. 6, middle panel) and sEng (FIG. 6, right-hand panel).

There have been a number of studies investigating the VEGF family of proteins in pre-eclampsia [References 4, 17, 18], which have suggested that they can play a role in its pathophysiology [References 19, 20]. The data presented above show that the total VEGF levels measured by EIA are consistent with those previously measured using this assay methodology [Reference 11] and by those using an independent method, the radioimmunoassay (RIA) [Reference 10].

In contrast, the above ELISA results from the same samples gave much lower readings, consistent with previous ELISA reports of plasma VEGF [Reference 21]. These experiments therefore highlight the previously reported discrepancy between measurements of total circulating VEGF in plasma by commercial ELISAs compared with cEIA, or RIA [Reference 22].

The antibodies used in the ELISA are two monoclonals raised against the VEGF peptide sequence and thus can be raised against a similar or identical epitope. The ELISA appears to yield artificially low results, presumably as VEGF is bound by agents in plasma which prevent its detection by both antibodies simultaneously. sFlt-1 does not affect this ELISA when given as recombinant protein [Reference 15], but the effect of endoglin or other plasma constituents has not been tested. The discrepancy was particularly striking after measurement of $VEGF_{165}b$ levels, using an ELISA that detects plasma $VEGF_{165}b$ using two antibodies that have epitopes on completely separate parts of the antigen (VEGF) molecule.

Of the VEGF family, $VEGF_{165}$, the most widely studied form [Reference 6] is known to increase vascular leakage, induce vasodilatation and promote angiogenesis. Although this isoform is up-regulated in pre-eclampsia, its metabolic activities can be blocked by other proteins which bind to VEGF and inhibit its function. sFlt-1 and sEng both bind to VEGF and prevent it from exerting its physiological effects [Reference 23]. sFlt-1 is an anti-angiogenic molecule that is able to induce a pre-eclamptic-like syndrome of hypertension and proteinuria when administered to pregnant rats [Reference 7]. sEng is an anti-angiogenic protein that inhibits TGF (transforming growth factor) $\beta_1$ and $\beta_3$ signalling and increases the severity of pre-eclampsia occurring in pregnant rats treated with sFlt-1 [Reference 24]. However, neither molecule can be used clinically as a first trimester marker of pre-eclampsia as sFlt-1 levels are seen to rise only 5 weeks before the onset of the clinical disease [Reference 25], and sEng concentrations become elevated at 17 weeks of gestation [Reference 23].

In 2002, $VEGF_{165}b$ was identified in normal renal cortex, and subsequently shown to be present in many different tissues, and forms the majority of VEGF in tissues such as human colon [Reference 15] and vitreous [Reference 26]. $VEGF_{165}b$ is relatively down-regulated in many conditions, including prostate, renal, bowel, and skin cancers [References 12, 15, 25, 27, 28], diabetic retinopathy [Reference 26], Denys-Drash Syndrome [Reference 29] and in the placenta of patients with pre-eclampsia [Reference 14]. The mechanisms underlying these changes in expression are still under investigation, but the reduction is associated with excess angiogenesis. $VEGF_{165}b$ has been shown to be anti-angiogenic in animal models of $VEGF_{165}$-induced blood vessel growth in the cornea [Reference 30], mouse subcutaneous tissue [Reference 31] and rat mesentery [Reference 27], and inhibits physiological [Reference 32] and pathological [References 15, 30, 32] angiogenesis. Studies have also shown that $VEGF_{165}b$ transiently, but not chronically, increases hydraulic conductivity [Reference 13].

The results described herein indicate that $VEGF_{165}b$ fails to be up-regulated in the first trimester in those pregnancies that will later be complicated by pre-eclampsia. It can be concluded that $VEGF_{165}b$ is a clinically useful marker for increased pre-eclampsia risk, providing for instance a guide to commencement of first trimester oral aspirin therapy, as this decreases the incidence of pre-eclampsia by 15% [Reference 33].

In summary, pre-eclampsia is a pregnancy related condition characterised by hypertension, proteinuria and endothelial dysfunction. $VEGF_{165}b$, formed by alternative splicing of vascular endothelial growth factor (VEGF) pre-mRNA inhibits its $VEGF_{165}$ mediated vasodilatation and angiogenesis, but has not been quantified in pregnancy. In the tests described herein, ELISAs were used to measure mean±S.E.M. plasma $VEGF_{165}b$, sEng and sFlt-1. At 12 weeks of gestation, the plasma $VEGF_{165}b$ concentration was significantly up-regulated in plasma from women who maintained normal blood pressure throughout their pregnancy (normotensive group 4.90±1.6 ng/ml, P<0.01, as determined using a Mann-Whitney U test) compared with non-pregnant women (0.40±0.22 ng/ml). In contrast, in patients who later developed pre-eclampsia, $VEGF_{165}b$ levels were lower than in the normotensive group (0.467±0.21 ng/ml), but were no greater than non-pregnant women. At term, plasma $VEGF_{165}b$ concentrations was greater than normal in both pre-eclamptic (3.75±2.24 ng/ml) and normotensive (10.6 ng/ml±3.84 ng/ml; P>0.1 compared with pre-eclampsia) pregnancies. Patients with a lower than median plasma $VEGF_{165}b$ at 12 weeks had elevated sFlt-1 and sEng pre-delivery. Concentrations of sFlt-1 (1.20±0.07 and 1.27±0.18 ng/ml) and sEng (4.4±0.18 and 4.1±0.5 ng/ml) were similar at 12 weeks of gestation in the normotensive and pre-eclamptic groups respectively. Plasma $VEGF_{165}b$ levels were elevated in pregnancy, but this increase is delayed in women that subsequently develop pre-eclampsia. Low $VEGF_{165}b$ is therefore a clinically useful plasma marker for increased risk of pre-eclampsia.

REFERENCES

1. Khan, K. S., Wojdyla, D., Say, L., Gulmezoglu, A. M. and Van Look, P. F. (2006) WHO analysis of causes of maternal death: a systematic review. Lancet. April 1; 367(9516), 1066-1074.

2. Zhou, Y., Damsky, C. H. and Fisher, S. J. (1997) Preeclampsia is associated with failure of human cytotrophoblasts to mimic a vascular adhesion phenotype. One cause of defective endovascular invasion in this syndrome? J Clin Invest. May 1; 99(9), 2152-2164.

3. Maynard, S. E., Venkatesha, S., Thadhani, R. and Karumanchi, S. A. (2005) Soluble Fms-like tyrosine kinase 1 and endothelial dysfunction in the pathogenesis of preeclampsia. Pediatr Res. May; 57(5 Pt 2), 1R-7R.

4. Levine, R. J., Maynard, S. E., Qian, C., Lim, K. H., England, L. J., Yu, K. F., Schisterman, E. F., Thadhani, R., Sachs, B. P., Epstein, F. H., Sibai, B. M., Sukhatme, V. P. and Karumanchi, S. A. Circulating angiogenic factors and the risk of preeclampsia. (2004) N Engl J Med. February 12; 350(7), 672-683.

5. Baumwell, S., Karumanchi, S. A. (2007) Pre-eclampsia: clinical manifestations and molecular mechanisms. Nephron Clin Pract. 2007; 106(2), c72-81.

6. Ferrara, N. (2004) Vascular endothelial growth factor: basic science and clinical progress. Endocr Rev. August; 25(4), 581-611.

7. Maynard, S. E., Min, J. Y., Merchan, J., Lim, K. H., Li, J., Mondal, S., Libermann, T. A., Morgan, J. P., Sellke, F. W., Stillman, I. E., Epstein, F. H., Sukhatme, V. P. and Karumanchi, S. A. (2003) Excess placental soluble fms-like tyrosine kinase 1 (sFlt1) may contribute to endothelial dysfunction, hypertension, and proteinuria in preeclampsia. J Clin Invest.; 111(5), 649-658.

8. Livingston, J. C., Chin, R., Haddad, B., McKinney, E. T., Ahokas, R. and Sibai, B. M. (2000) Reductions of vascular endothelial growth factor and placental growth factor concentrations in severe preeclampsia. Am J Obstet Gynecol. December; 183(6), 1554-1557.

9. Lyall, F., Young, A., Boswell, F., Kingdom, J. C. and Greer, I. A. (1997) Placental expression of vascular endothelial growth factor in placentae from pregnancies complicated by pre-eclampsia and intrauterine growth restriction does not support placental hypoxia at delivery. Placenta. May; 18(4), 269-276.

10. McKeeman, G. C., Ardill, J. E., Caldwell, C. M., Hunter, A. J. and McClure, N. (2004) Soluble vascular endothelial growth factor receptor-1 (sFlt-1) is increased throughout gestation in patients who have preeclampsia develop. Am J Obstet Gynecol. October; 191(4), 1240-1246.

11. Lee, E. S., Oh, M. J., Jung, J. W., Lim, J. E., Seol, H. J., Lee, K. J. and Kim, H. J. (2007) The levels of circulating vascular endothelial growth factor and soluble Flt-1 in pregnancies complicated by preeclampsia. J Korean Med Sci. February; 22(1), 94-98.

12. Bates, D. O., Cui, T. G., Doughty, J. M., Winkler, M., Sugiono, M., Shields, J. D., Peat, D., Gillatt, D. and Harper, S. J. (2002) VEGF165b, an inhibitory splice variant of vascular endothelial growth factor, is down-regulated in renal cell carcinoma. Cancer Res. July 15; 62(14), 4123-4131.

13. Glass, C. A., Harper, S. J. and Bates, D. O. (2006) The anti-angiogenic VEGF isoform $VEGF_{165}b$ transiently increases hydraulic conductivity, probably through VEGF receptor 1 in vivo. J Physiol. April 1; 572(Pt 1), 243-257.

14. Bates, D. O., MacMillan, P. P., Manjaly, J. G., Qiu, Y., Hudson, S. J., Bevan, H. S., Hunter, A. J., Soothill, P. W., Read, M., Donaldson, L. F. and Harper, S. J. (2006) The endogenous anti-angiogenic family of splice variants of VEGF, VEGFxxxb, are down-regulated in pre-eclamptic placentae at term. Clin Sci (Lond). May; 110(5), 575-585.

15. Varey, A. H., Rennel, E. S., Qiu, Y., Bevan, H. S., Perrin, R. M., Raffy, S., Dixon, A. R., Paraskeva, C., Zaccheo, O., Hassan, A. B., Harper, S. J. and Bates, D. O. (2008) VEGF (165)b, an antiangiogenic VEGF-A isoform, binds and inhibits bevacizumab treatment in experimental colorectal carcinoma: balance of pro- and antiangiogenic VEGF-A isoforms has implications for therapy. Br J Cancer. April 22; 98(8), 1366-1379.

16. Alberry, M., Soothill, P. W. (2007) Management of fetal growth restriction. Arch Dis Child Fetal Neonatal Ed. January; 92(1), F62-F67.

17. Brockelsby, J., Hayman, R., Ahmed, A., Warren, A., Johnson, I. and Baker, P. (1999) VEGF via VEGF receptor-1 (Flt-1) mimics preeclamptic plasma in inhibiting uterine blood vessel relaxation in pregnancy: implications in the pathogenesis of preeclampsia. Lab Invest. September; 79(9), 1101-1111.

18. Sgambati, E., Marini, M., Zappoli, Thyrion, G. D., Parretti, E., Mello, G., Orlando, C., Simi, L., Tricarico, C., Gheri, G. and Brizzi, E. (2004) VEGF expression in the placenta from pregnancies complicated by hypertensive disorders. Br J Obstet Gynaecol. 2004 June; 111(6), 564-570.

19. Li, Z., Zhang, Y., Ying, Ma, J., Kapoun, A. M., Shao, Q., Kerr, I., Lam, A., O'Young, G., Sannajust, F., Stathis, P., Schreiner, G., Karumanchi, S. A., Protter, A. A. and Pollitt, N. S. (2007) Recombinant vascular endothelial growth factor 121 attenuates hypertension and improves kidney damage in a rat model of preeclampsia. Hypertension. October; 50(4), 686-692.

20. Murakami, Y., Kobayashi, T., Omatsu, K., Suzuki, M., Ohashi, R., Matsuura, T., Sugimura, M., and Kanayama, N. (2005) Exogenous vascular endothelial growth factor can induce preeclampsia-like symptoms in pregnant mice. Semin. Thromb. Hemost. June; 31(3), 307-313.

21. Nadar, S. K., Karalis, I., AlYemeni, E., Blann, A. D. and Lip, G. Y. (2005) Plasma markers of angiogenesis in pregnancy induced hypertension. Thromb Haemost. November; 94(5), 1071-1076.

22. Anthony, F. W., Evans, P. W., Wheeler, T. and Wood, P. J. (1997) Variation in detection of VEGF in maternal serum by immunoassay and the possible influence of binding proteins. Ann Clin Biochem. May; 34(Pt 3), 276-280.

23. Levine, R. J., Lam, C., Qian, C., Yu, K. F., Maynard, S. E., Sachs, B. P., Sibai, B. M., Epstein, F. H., Romero, R., Thadhani, R. and Karumanchi, S. A.; CPEP Study Group. (2006) Soluble endoglin and other circulating antiangiogenic factors in preeclampsia. N Engl J Med. September 7; 355(10), 992-1005.

24. Venkatesha, S., Toporsian, M., Lam, C., Hanai, J., Mammoto, T., Kim, Y. M., Bdolah, Y., Lim, K. H., Yuan, H. T., Libermann, T. A., Stillman, I.E., Roberts, D., D'Amore, P. A., Epstein, F. H., Sellke, F. W., Romero, R., Sukhatme, V. P., Letarte, M. and Karumanchi, S. A. (2006) Soluble endoglin contributes to the pathogenesis of preeclampsia. Nat Med. June; 12(6), 642-649.

25. Levine, R. J., Maynard, S. E., Qian, C., Lim, K. H., England, L. J., Yu, K. F., Schisterman, E. F., Thadhani, R., Sachs, B. P., Epstein, F. H., Sibai, B. M., Sukhatme, V. P. and Karumanchi, S. A. (2004) Circulating angiogenic factors and the risk of preeclampsia. N Engl J Med. February 12; 350(7), 672-683.

26. Perrin, R. M., Konopatskaya, O., Qiu, Y., Harper, S., Bates, D. O. and Churchill, A. J. (2005) Diabetic retinopathy is associated with a switch in splicing from anti- to pro-angiogenic isoforms of vascular endothelial growth factor. Diabetologia. November; 48(11), 2422-2427.

27. Woolard, J., Wang, W. Y., Bevan, H. S., Qiu, Y., Morbidelli, L., Pritchard-Jones, R. O., Cui, T. G., Sugiono, M., Waine, E., Perrin, R., Foster, R., Digby-Bell, J., Shields, J. D., Whittles, C. E., Mushens, R. E., Gillatt, D. A., Ziche, M., Harper, S. J. and Bates, D. O. (2004) $VEGF_{165}b$, an inhibitory vascular endothelial growth factor splice variant: mechanism of action, in vivo effect on angiogenesis and endogenous protein expression. Cancer Res. November 1; 64(21), 7822-7835.

28. Pritchard-Jones, R. O., Dunn, D. B., Qiu, Y., Varey, A. H., Orlando, A., Rigby, H., Harper, S. J. and Bates, D. O. (2007) Expression of VEGF(xxx)b, the inhibitory isoforms of VEGF, in malignant melanoma. Br J Cancer. July 16; 97(2), 223-230.

29. Schumacher, V. A., Jeruschke, S., Eitner, F., Becker, J. U., Pitschke, G., Ince, Y., Miner, J. H., Leuschner, I., Engers, R., Everding, A. S., Bulla, M. and Royer-Pokora, B. (2007) Impaired glomerular maturation and lack of VEGF165b in Denys-Drash syndrome. J Am Soc Nephrol. March; 18(3), 719-729.

30. Konopatskaya, O., Churchill, A. J., Harper, S. J., Bates, D. O. and Gardiner, T. A. (2006) VEGF165b, an endogenous C-terminal splice variant of VEGF, inhibits retinal neovascularization in mice. Mol Vis. May 26; 12, 626-632.

31. Rennel, E., Waine, E., Guan, H., Schiller, Y., Leenders, W., Woolard, J., Sugiono, M., Gillatt, D., Kleinerman, E., Bates, D. O. and Harper, S. J. (2008) The endogenous anti-angiogenic VEGF isoform, VEGF(165)b inhibits human tumour growth in mice. Br J Cancer. April 8; 98(7), 1250-1257.

32. Qiu, Y., Bevan, H., Weeraperuma, S., Wratting, D., Murphy, D., Neal, C. R., Bates, D. O. and Harper, S. J. (2008) Mammary alveolar development during lactation is inhibited by the endogenous antiangiogenic growth factor isoform, VEGF165b. FASEB J. April; 22(4), 1104-1112.

33. Duley, L., Henderson-Smart, D., Knight, M. and King, J. (2001) Antiplatelet drugs for prevention of pre-eclampsia and its consequences: systematic review. Br Med J. February 10; 322(7282), 329-333.

The foregoing broadly describes the present invention without limitation. Variations and modifications as will be readily apparent to those skilled in the art are intended to be within the scope of the present invention as defined in and by the appended claims.

What is claimed is:

1. A method for detecting a risk of a pregnant female mammal developing pre-eclampsia or a complication linked thereto, or of a fetus of the pregnant female mammal developing a fetal or neonatal deficiency linked to maternal pre-eclampsia, comprising:
   detecting the level of a $VEGF_{xxx}b$ in a sample from the pregnant female mammal before the end of the second trimester of the mammal's pregnancy;
   comparing the detected level with a reference level, wherein a level in the sample of the pregnant female mammal below the reference level is indicative of a risk of the pregnant female mammal developing pre-eclampsia or a complication linked thereto or of the fetus developing the fetal or neonatal deficiency linked to maternal pre-eclampsia; and
   increasing the level of a $VEGF_{xxx}b$ in the pregnant female mammal when the detected level is below the reference level by administering a $VEGF_{xxx}b$ active agent to the pregnant female mammal.

2. The method according to claim 1, wherein the mammal is a human.

3. The method according to claim 2, wherein the $VEGF_{xxx}b$ is $VEGF_{165}b$.

4. The method according to claim 1, wherein the detection of the level of the $VEGF_{xxx}b$ is performed on a sample of a body fluid taken from the pregnant female mammal.

5. The method according to claim 4, wherein the body fluid is blood serum.

6. The method according to claim 1, wherein the level of $VEGF_{xxx}b$ is detected at less than about 16 weeks of gestation.

7. The method according to claim 1, wherein the level of $VEGF_{xxx}b$ is detected at up to about 12 weeks of gestation.

8. The method according to claim 1, wherein the level of $VEGF_{xxx}b$ is detected at about 12 weeks of gestation.

9. The method according to claim 1, wherein the pre-eclampsia is severe pre-eclampsia or early-onset pre-eclampsia.

10. The method according to claim 1, wherein the reference level is an average derived from population studies on gestationally age-matched pregnant females who did not develop pre-eclampsia.

11. The method according to claim 1, wherein the detection of the level of the $VEGF_{xxx}b$ is performed using an immunoassay.

12. The method according to claim 11, wherein the immunoassay is an ELISA.

13. The method according to claim 1, wherein the $VEGF_{xxx}b$ is $VEGF_{165}b$ and the reference level is at least 0.5 ng/ml serum $VEGF_{165}b$ at less than 24 weeks of gestation as measured by ELISA.

* * * * *